(12) United States Patent
Maile et al.

(10) Patent No.: US 8,428,713 B2
(45) Date of Patent: Apr. 23, 2013

(54) IMPLANTABLE DEFIBRILLATION OUTPUT CIRCUIT

(75) Inventors: Keith R. Maile, New Brighton, MN (US); William J. Linder, Golden Valley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 23 days.

(21) Appl. No.: 13/041,970

(22) Filed: Mar. 7, 2011

(65) Prior Publication Data

US 2011/0224747 A1 Sep. 15, 2011

Related U.S. Application Data

(60) Provisional application No. 61/311,851, filed on Mar. 9, 2010.

(51) Int. Cl.
*A61N 1/39* (2006.01)
(52) U.S. Cl.
USPC .............................................................. 607/5
(58) Field of Classification Search .................. 607/4, 5
See application file for complete search history.

(56) References Cited

U.S. PATENT DOCUMENTS

| 4,800,883 A | 1/1989 | Winstrom |
|---|---|---|
| 4,821,723 A | 4/1989 | Baker, Jr. et al. |
| 4,823,796 A | 4/1989 | Benson |
| RE34,879 E | 3/1995 | Bocchi et al. |
| 5,591,218 A | 1/1997 | Jacobson |
| 5,626,619 A | 5/1997 | Jacobsen et al. |
| 5,645,572 A | 7/1997 | Kroll et al. |
| 5,782,880 A | 7/1998 | Lahtinen et al. |
| 6,035,235 A * | 3/2000 | Perttu et al. .......................... 607/5 |
| 6,208,898 B1 | 3/2001 | Gliner et al. |
| 6,668,193 B2 | 12/2003 | Ware et al. |
| 7,211,884 B1 | 5/2007 | Davis et al. |
| 7,522,957 B2 | 4/2009 | Ostroff |
| 2002/0072769 A1 | 6/2002 | Silvian et al. |
| 2002/0161406 A1 | 10/2002 | Silvian |
| 2003/0088279 A1 | 5/2003 | Rissmann et al. |
| 2003/0088282 A1 | 5/2003 | Ostroff |
| 2005/0288714 A1 | 12/2005 | Ostroff |
| 2009/0157132 A1 | 6/2009 | Linder et al. |
| 2009/0210021 A1 | 8/2009 | Ostroff |

OTHER PUBLICATIONS

"International Application Serial No. PCT/US2011/027388, International Search Report mailed Jun. 17, 2011", 4 pgs.
"International Application Serial No. PCT/US2011/027388, Written Opinion mailed Jun. 17, 2011", 8 pgs.

* cited by examiner

*Primary Examiner* — George Evanisko
(74) *Attorney, Agent, or Firm* — Schwegman Lundberg & Woessner, P.A.

(57) ABSTRACT

An implantable defibrillation circuit can include an output circuit. The output circuit can include a first switch configured to controllably connect a first supply node to a first output node, a second switch configured to controllably connect a second supply node to the first output node through a first rectifier, and the second switch can be configured to inhibit the first switch from connecting the first supply node to the first output node when the second supply node is connected to the first output node through the second switch. In an example, the first and second switches can include insulated gate bipolar transistors.

20 Claims, 5 Drawing Sheets

IMPLANTABLE DEFIBRILLATION OUTPUT CIRCUIT

CROSS REFERENCE TO RELATED APPLICATIONS

This application claims the benefit under 35 U.S.C. 119(e) to Maile et al., U.S. Provisional Patent Application Ser. No. 61/311,851, entitled "Implantable Defibrillation Output Circuit", filed on Mar. 9, 2010, which is hereby incorporated herein by reference in its entirety.

BACKGROUND

A heart can be considered the center of a circulatory system within a body. For example, the heart can take deoxygenated blood from elsewhere in the body and provide it to the lungs to be oxygenated. The heart can then supply the oxygenated blood from the lungs to other parts of the body. In a healthy heart, each chamber can contract in a coordinated fashion, such as to provide adequate circulation of oxygenated blood and nutrients to sustain the body.

The heart can be affected by a variety of physical and electrical abnormalities. Physical abnormalities can include, among other things, enlarging of the heart, sometimes associated with ischemia. Electrical abnormalities can include, among other things, various arrhythmias, such as due to infarcts, congenital defects, aging, or one or more other factors. Certain arrhythmias can be life threatening, such as including a ventricular tachyarrhythmia or ventricular fibrillation. In some patients, such life threatening arrhythmias can be detected and terminated using low-energy electrical impulses, such as provided by an implantable pulse generator. Such low-energy electrical impulses can include anti-tachyarrhythmia pacing (ATP), but such pacing is not always indicated or effective for termination of a particular arrhythmia.

In cases where ATP is not indicated, or is ineffective, a defibrillation countershock can be provided, such as by an automatic implantable cardioverter defibrillator (AICD). An AICD can provide the defibrillation countershock subcutaneously, epicardially, or using one or more intravascularly-deliverable implantable leads such as located within or near the heart or vasculature.

Overview

In an example, an implantable cardiac function management device can include an implantable defibrillation circuit configured to provide a defibrillation shock. The defibrillation circuit can include a power supply, such as including a switching converter or flyback circuit, or the like, to provide a specified stored energy for delivery to a patient as a defibrillation countershock having a specified waveform. In an example, the power supply can operate using a relatively low input voltage (e.g., around 2-5 volts, such as provided by a battery or provided through one or more regulated power supplies). In an example, the energy for defibrillation can be stored using one or more high-voltage capacitors, such as connected in series, or in another configuration (e.g., a capacitor "stack"). During operation, the power supply can pump charge into the capacitor stack, to store energy at a peak voltage at or beyond the input voltage (e.g., using a boost configuration, or the like). The energy stored in the one or more capacitors can then be used to provide a defibrillation countershock having a specified waveform including a relatively high peak voltage (e.g., from less than 40 volts to more than 780 volts).

In an example, the defibrillation circuit can also include an implantable output circuit or output "bridge," to controllably connect the one or more high-voltage capacitors to two or more electrodes in contact with patient tissue, such as one or more implantable electrodes located in the pectoral region, subcutaneously, or intravascularly. During delivery of the defibrillation countershock, the output circuit can adjust a polarity of the applied voltage, such as provided by the one or more capacitors, such as to obtain a mono-phasic, bi-phasic, or other wave shape. In an example, the output circuit can be used to select a specified combination of electrodes to provide the countershock through a specified "pathway" or "vector." For example, the defibrillation energy can be provided between two electrodes located on or within one or more intravascularly-deliverable lead assemblies, or between one or more electrodes and a housing of the implantable cardiac function management device.

In an example, the defibrillation output circuit can include a first switch configured to controllably connect a first supply node to a first output node, a second switch configured to controllably connect a second supply node to the first output node through a first rectifier, and the second switch can be configured to inhibit the first switch from connecting the first supply node to the first output node when the second supply node is connected to the first output node through the second switch. The present inventors have recognized, among other things, that having a second switch inhibiting a first switch can reduce an overall complexity of the output circuit, such as by eliminating a need for a separate control switch to inhibit the first switch. Thus, the second switch can both provide a path (e.g., a return path) for defibrillation countershock therapy current, while also controlling a state of the first switch. In an example, the first and second switches can include insulated gate bipolar transistors (IGBTs), also called insulated gate bipolar junction transistors (IGBJTs). The present inventors have also recognized that using IGBTs can reduce the cost or complexity of the output circuit, or to avoid other difficulties, as compared to using one or more other types of switching components. In a medical electronic assembly, such as an implantable device, reduction of cost or complexity may allow a larger population of patients to receive devices, since such reduction may motivate public or private insurers to more readily reimburse care-givers or device manufacturers for the costs of assembling, distributing, and implanting such devices.

Example 1 can include an implantable defibrillation circuit. In Example 1, the implantable defibrillation circuit optionally includes an implantable output circuit including a first switch configured to controllably connect a first supply node to a first output node, a second switch configured to controllably connect a second supply node to the first output node through a first rectifier, the second switch configured to inhibit the first switch from connecting the first supply node to the first output node when the second supply node is connected to the first output node through the second switch, and the first output node configured to be coupled to a first implantable electrode.

In Example 2, the subject matter of Example 1 optionally includes a first switch including a control input configured to control a conductive state of the first switch using a voltage, and the second switch can be configured to controllably connect the second supply node to the control input of the first switch.

In Example 3, the subject matter of any one or more of Examples 1 through 2 optionally includes a filter circuit coupled to the control input, the filter circuit configured to adjust at least one of a rise-time or a fall-time of the first switch, at least in part using a capacitance of the control input.

In Example 4, the subject matter of any one or more of Examples 1 through 3 optionally includes an energy source configured to provide energy via the first and second supply nodes at a specified initial voltage at the first supply node that is greater than or equal to 780 volts with respect to the second supply node.

In Example 5, the subject matter of any one or more of Examples 1 through 4 optionally includes an implantable output circuit that can include a third switch configured to controllably connect the first supply node to a second output node, a fourth switch configured to controllably connect the second supply node to the second output node through a second rectifier, the fourth switch configured to inhibit the third switch from connecting the first supply node to the second output node when the second supply node is connected to the second output node through the fourth switch, and the second output node configured to be coupled to a second implantable electrode.

In Example 6, the subject matter of any one or more of Examples 1 through 5 optionally includes respective first, second, third, and fourth switches each comprising an insulated gate bipolar transistor (IGBT).

In Example 7, the subject matter of any one or more of Examples 1 through 6 optionally includes an implantable output is configured to provide a defibrillation waveform across the first and second output nodes, the defibrillation waveform having a specified polarity when only one of the first or second switches is turned on and only one of the third or fourth switches is turned on.

In Example 8, the subject matter of any one or more of Examples 1 through 7 optionally includes an implantable output circuit configured to provide a defibrillation waveform having a first polarity during a first portion of the defibrillation waveform and a second opposite polarity during a second portion of the defibrillation waveform.

In Example 9, the subject matter of any one or more of Examples 1 through 8 optionally includes first, second, third, and fourth switches that can each include a respective control input, and each respective control input can be configured to be coupled to a respective control circuit, such as included as a portion of an integrated circuit, using an un-isolated electrical coupling.

In Example 10, the subject matter of any one or more of Examples 1 through 9 optionally includes first, second, third, and fourth switches that can each include a separate semiconductor die positioned on a commonly-shared non-semiconductor substrate.

In Example 11, the subject matter of any one or more of Examples 1 through 10 optionally includes an implantable lead including the first electrode, the implantable lead configured to couple the first output node to the first electrode.

In Example 12, the subject matter of any one or more of Examples 1 through 10 optionally includes a housing including a conductive portion, and the conductive portion can include the first implantable electrode.

Example 13 can include an implantable defibrillation circuit. Example 13 can optionally include the subject matter of any one or more of Examples 1-12. In Example 13, the implantable defibrillation circuit optionally includes an implantable output circuit including a first switch having a control input configured to control a conductive state of the first switch using a voltage, the first switch configured to controllably connect a first supply node to a first output node, a second switch configured to controllably connect a second supply node to the first output node through a first rectifier and configured to controllably connect the second supply node to the control input of the first switch, the second switch configured to inhibit the first switch from connecting the first supply node to the first output node when the second supply node is connected to the first output node through the second switch, the first output node configured to be coupled to a first implantable electrode.

In Example 14, the subject matter of any one or more of Examples 1 through 13 optionally includes a housing including a conductive portion, the conductive portion optionally including the first implantable electrode.

Example 15 can include a method of controlling delivery of a defibrillation. Example 15 can optionally include the subject matter of any one or more of Examples 1-14. Example 15 optionally includes controlling a connection between a first supply node and a first output node using a first switch, controlling a connection between a second supply node and the first output node using a second switch, using the second switch, inhibiting the first switch from connecting the first supply node to the first output node when the second supply node is connected to the first output node through the second switch, and providing a defibrillation waveform to a heart using at least the first output node.

In Example 16, the subject matter of any one or more of Examples 1 through 15 optionally includes controlling the connection between the first output node and the second supply nodes including providing a rectification in a path between the second supply node and the first output.

In Example 17, the subject matter of any one or more of Examples 1 through 16 optionally includes controlling a conductive state of the first switch using the second switch including controllably connecting the second supply node to a control input of the first switch using a commonly-shared path including the first output node, the second supply node, and a first rectifier.

In Example 18, the subject matter of any one or more of Examples 1 through 17 optionally includes controlling a connection between the first supply node and a second output node using a third switch, controlling a connection between the second supply node and the second output node using a fourth switch, using the fourth switch to inhibit the third switch from connecting the first supply node to the second output node when the second supply node is connected to the second output node through the third switch, and the providing the defibrillation to the heart optionally including using the second output node.

In Example 19, the subject matter of any one or more of Examples 1 through 18 optionally includes providing the defibrillation waveform to the heart including providing a defibrillation waveform across the first and second output nodes, the defibrillation waveform including a portion having a specified polarity when only one of the first or second switches is turned on, and when only one of the third or fourth switches is turned on.

In Example 20, the subject matter of any one or more of Examples 1 through 19 optionally includes providing the defibrillation waveform to the heart including providing a defibrillation waveform having a first polarity during a first portion of the defibrillation waveform and a second opposite polarity during a second portion of the defibrillation waveform.

Example 21 can include, or can optionally be combined with any portion or combination of any portions of any one or more of Examples 1-20 to include, subject matter that can include means for performing any one or more of the functions of Examples 1-20, or a machine-readable medium including instructions that, when performed by a machine, cause the machine to perform any one or more of the functions of Examples 1-20.

The examples discussed herein can include apparatus that can be implantable, such as shown in the examples of FIGS. 1-2, 3A-B, 4A-B and 5. However, in an example, such apparatus can also be included as a portion, part, or component of an external defibrillator apparatus, such as an automatic external defibrillator (AED) or another external assembly.

These examples can be combined in any permutation or combination. This overview is intended to provide an overview of subject matter of the present patent application. It is not intended to provide an exclusive or exhaustive explanation of the invention. The detailed description is included to provide further information about the present patent application. The phrases "defibrillation," "defibrillation countershock," "shock," and "cardioversion" can be used interchangeably. In an example, cardioversion can refer to delivery of a shock to convert a non-fibrillating arrhythmia to a normal sinus rhythm, such as can be triggered or delivered synchronously to intrinsic cardiac electrical activity.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
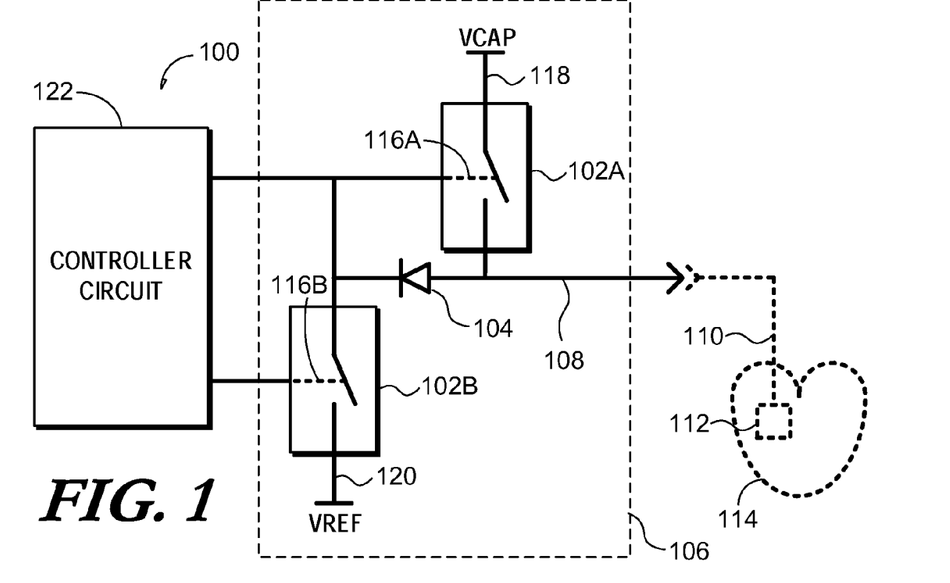
FIG. 1 illustrates generally an example of a portion of an implantable defibrillation circuit including a first switch and a second switch.

FIG. 1 illustrates generally an example of a portion of an implantable defibrillation circuit 100 that can include an implantable defibrillation output circuit 106, such as including a first switch 102A and a second switch 102B. In FIG. 1, the first switch 102A can include a first control input 116A, such as connected to a first control output of a controller circuit 122. In FIG. 1, the second switch 102B can include a second control input 116B, such as connected to a second control output of a controller 122.

In an example, the controller circuit 122 and defibrillation output circuit 106 can be included as a portion or part of an implantable cardiac function management device. For example, the implantable cardiac function management device can include one or more power supplies, such as a switch-mode voltage converter or a flyback circuit, or the like, to provide a specified stored energy for delivery to a patient as a defibrillation countershock having a specified waveform. In an example, the power supply can operate using a relatively low input voltage (e.g., around 2-5 volts, such as provided by a battery). In an example, the energy for defibrillation (e.g., from less than 0.1 Joules to more than 41 Joules) can be stored using one or more high-voltage capacitors, such as connected in series, or in another configuration (e.g., a capacitor "stack"). During operation, the power supply can pump charge into the capacitor stack, to store energy at a peak voltage at or beyond the input voltage (e.g., using a boost configuration, or the like).

Figure 4A:
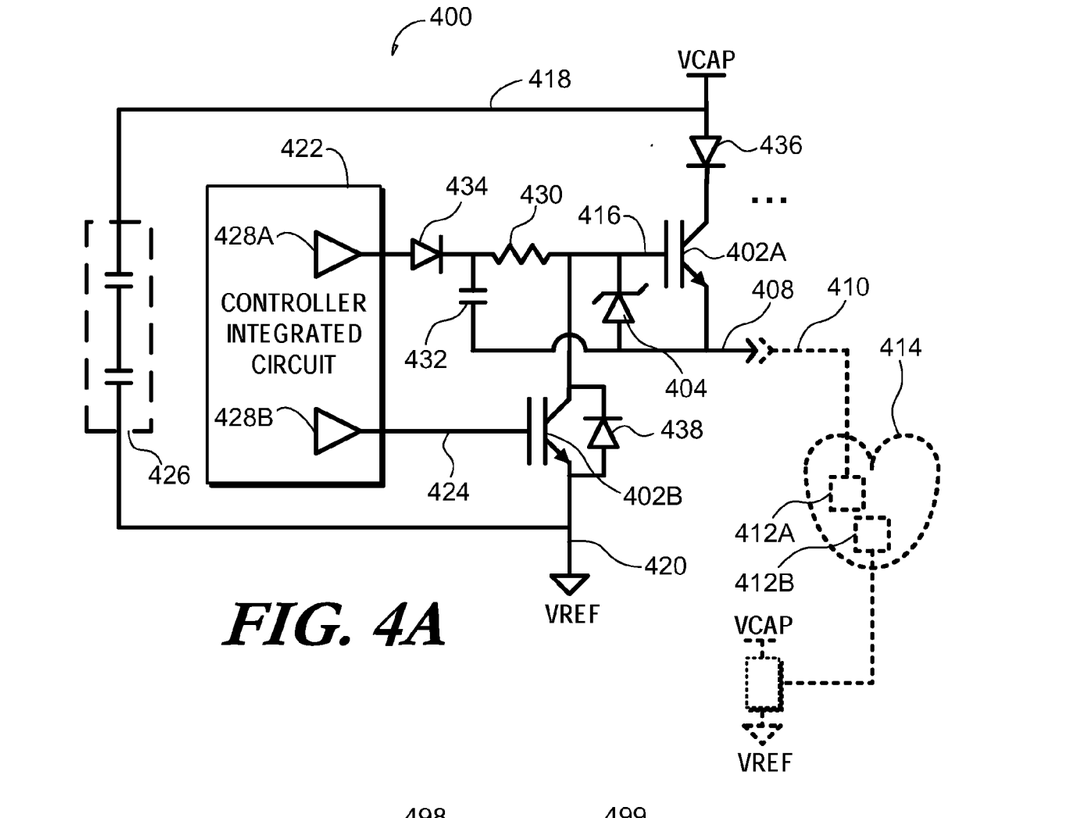
FIGS. 4A-B illustrate generally an example of a portion of an implantable defibrillation circuit including a first switch and a second switch, and an un-isolated connection to one or more control outputs included as a portion of a controller integrated circuit.

The energy stored in the one or more capacitors can then be used as an energy source to provide a defibrillation countershock having a specified waveform including a relatively high peak voltage (e.g., from less than 40 volts to more than 780 volts). In an example, the first or second switches 102A-B can be selectively opened and closed by the controller 122 to connect an output node 108 to a VCAP node 118 or to a VREF node 120. For example, VCAP can be connected to a first supply node, (e.g., a positive terminal of a capacitor stack), and VREF can be connected to second supply node (e.g., a negative terminal or return connection) of the capacitor stack), such as shown in FIG. 4A. In an example, the output node 108 can be connected to an implantable lead 110 (e.g., a subcutaneous lead, an intravascularly-delivered lead, etc.), such as including an implantable electrode 112 located within or near a heart 114 (e.g., an electrode included along the length of the lead, a subcutaneous patch, an epicardial patch, etc.).

In an example, a rectifier 104 or other component (e.g., a diode, a transistor or other semiconductor such as connected in a diode-like configuration) can permit current to flow in one direction (e.g., from the output node 108 toward VREF), but can almost completely block current flow in the opposite direction, such as up to a specified reverse breakdown voltage. In an example, the first switch 102A can be inhibited from connecting VCAP to the output node 108 when the second switch 102B is closed, such as using a voltage-controlled input for the first control input 116A. Such a voltage-controlled input can open the corresponding switch in response to a logic "low" voltage level, such as around 0V with respect to other nodes, and can close the switch in response to a logic "high" level, such as 12V, or another specified voltage, with respect to other nodes. For example, if VREF 120 is at or near a logic "low" level, such as near 0V with respect to other nodes in the defibrillation circuit 100, then the closing of switch 102B as controlled by the second control input 116B can coerce the first control input 116A low, inhibiting the first switch 102A from being closed. This inhibiting can prevent a short circuit from occurring between VCAP 118 and VREF 120. In the example of FIG. 1, the second switch 102B can be connected to the control input 116A of the first switch 102A, such as without any intervening rectifier or other components.

In an example, one or more of the first and second switches 102A-B can include a voltage-controlled semiconductor device, such as including a thyristor (e.g., a gate turn-off (GTO) thyristor such as a remote gate thyristor (RGT), or another thyristor such as including turn-on and turn-off controllability), a field-effect transistor (FET), an insulated gate bipolar transistor (IGBT), or the like. For example, the controller circuit 122 can include or can be connected to a drive circuit, such as shown in FIG. 4A, to condition the one or more control outputs to provide a specified drive signal for one or more of the first or second control inputs 116A-B of the first or second switches 102A-B (e.g., to providing level shifting of one or more of the control outputs, or to limit or adjust a rise-time or a fall-time of the specified drive signal, etc.).

Figure 2:
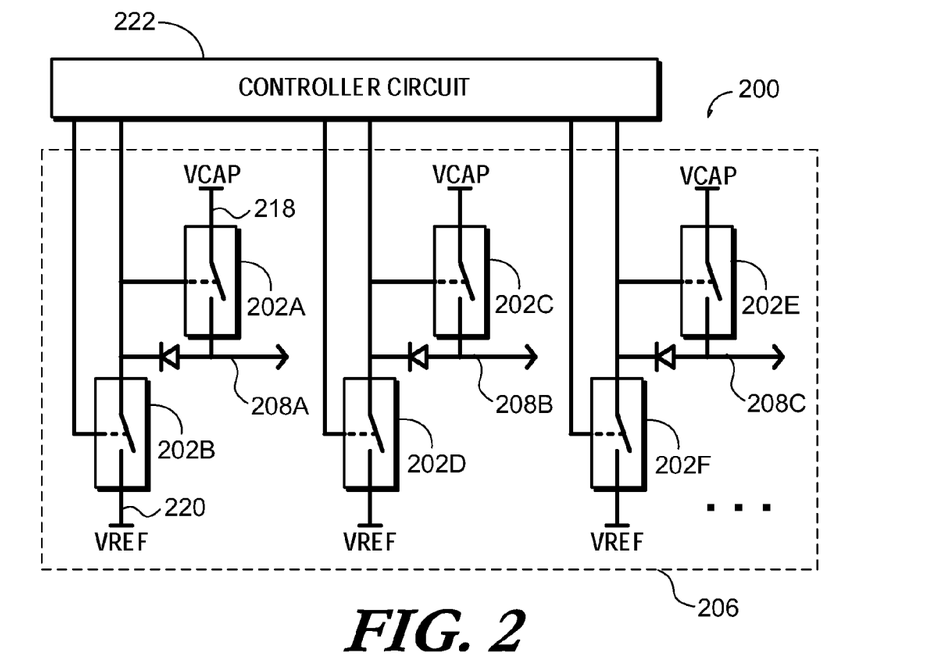
FIG. 2 illustrates generally an example of a portion of an implantable defibrillation circuit including multiple switches, such as for controllably connecting a first or second supply to one more outputs configured to be connected to one or more corresponding electrodes.

FIG. 2 illustrates generally an example of a portion of an implantable defibrillation circuit 200 that can include multiple switches, such as for controllably connecting a first or second supply node to respective output nodes configured to be connected to one or more corresponding electrodes. In an example, the defibrillation output circuit can include multiple output blocks, such as including one or more blocks each similar to the output circuit 106 of FIG. 1. For example, the defibrillation circuit 200 can include a first output node 208A, a second output node 208B, and a third output node 208C. A first supply node, such as a VCAP node 218 can be selectively connected to the first-third output nodes 208A-C using a respective first switch 202A, a third switch 202C, or a fifth switch 202E. Similarly, in an example, a second supply node, such as a VREF node 220, can be selectively connected to the first-third output nodes 208A-C using a respective second switch 202B, fourth switch 202D, or a sixth switch 202F. The respective first-third output nodes 208A-C can be connected to respective implantable electrodes, such as shown and discussed in FIGS. 3A-B.

In an example, the controller circuit 222 can control one or more of the first, second, third, fourth, fifth, or sixth switches to provide a specified defibrillation countershock waveform across a specified electrode combination such as discussed in U.S. patent application Ser. No. 12/332,497, entitled "Defibrillation Shock Output Circuit", filed Dec. 11, 2008, and assigned to Cardiac Pacemakers, Inc., which is herein incorporated by reference in its entirety, and specifically incorporating herein its discussion of providing a specified shock output "vector." Similar to FIG. 1, one or more of the second, fourth, or sixth switches 202B, 202D, or 202F, when closed (e.g., conducting), can be configured to inhibit the respective first, second, or fifth switch 202A, 202C, or 202E from connecting the first supply node (e.g., VCAP 218) to the respective first, second, or third output node 208A-C. While the example of FIG. 3 includes three respective output nodes, fewer or greater output nodes can also be used, such as controlled or driven by one or more output blocks such as including the output circuit 106 of FIG. 1.

Figure 3A:
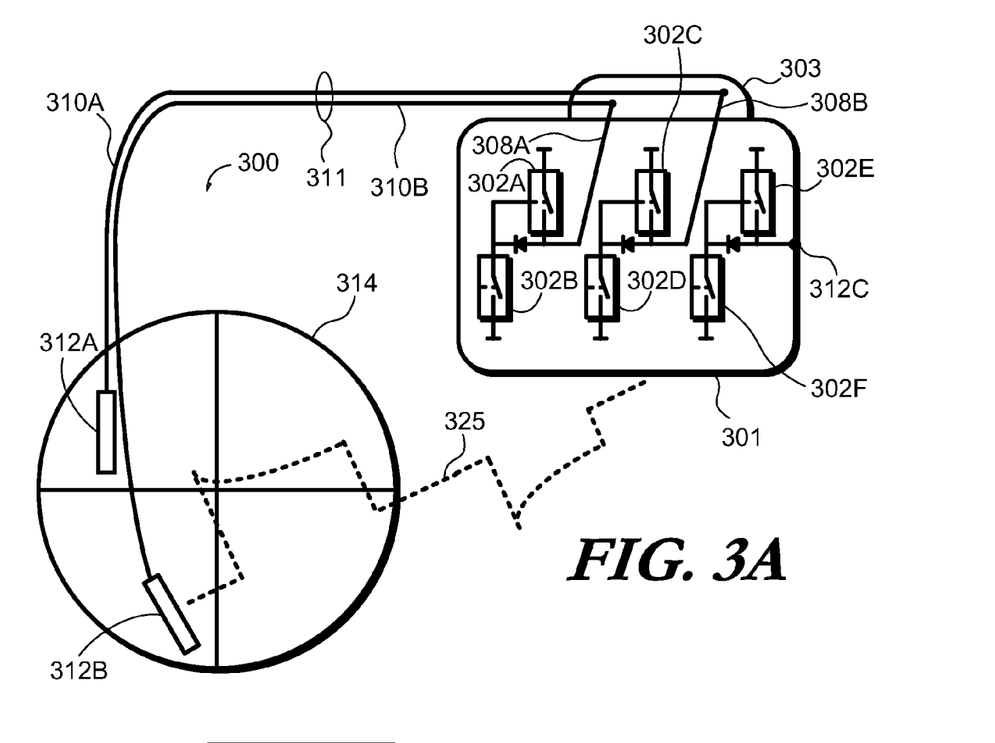
FIGS. 3A-B illustrate generally an example of an implantable medical device, showing a defibrillation output circuit including an illustrative example of a biphasic defibrillation shock waveform delivered across a specified electrode pair.
Figure 3B:
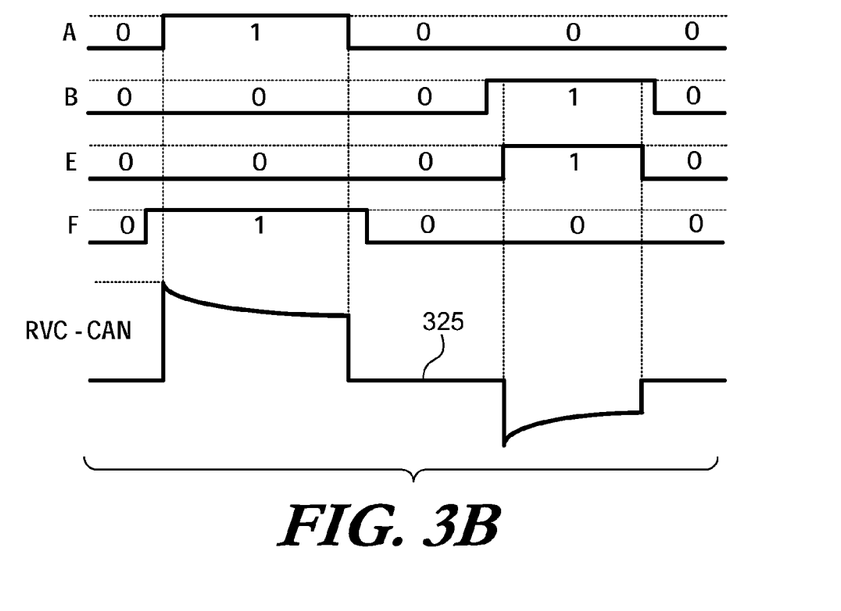

FIGS. 3A-B illustrate generally an example of a system 300 including an implantable medical device (IMD) 301 that can include an implantable defibrillation output circuit. FIG. 3A includes an illustrative example of a biphasic defibrillation shock waveform 325, such as delivered across a specified electrode pair, and FIG. 3B shows a diagram illustrating various switch states, such as used to obtain the specified defibrillation shock waveform 325. In FIG. 3A, IMD 301 can include a cardiac function management device, such as comprising an automatic implantable cardioverter defibrillator, among other capabilities. Similar to the examples of FIGS. 1-2, the implantable medical device 301 can include one or more output nodes configured to be connected to one or more corresponding electrodes, such as located within or near a heart 314. One or more other defibrillation waveforms can be provided using the system 300 of FIG. 3, such as one or more mono-phasic, bi-phasic, tri-phasic, or multi-phasic waveforms such as discussed in U.S. Pat. No. 4,800,883, entitled "Apparatus for generating multi-phasic defibrillation pulse waveform," filed Apr. 2, 1986, or U.S. Pat. No. 4,821,723, entitled "Biphasic waveforms for defibrillation," filed Apr. 18, 1989, both of which are assigned to Intermedics, Inc., and both of which are herein incorporated by reference in their respective entireties.

In an example, a first output 308A can be selectively connected to one of a first supply node or a second supply node, such as using a first switch 302A or a second switch 302B. For example, the first output 308A can be made available outside a housing of the IMD 301, such as via a feed-through, and connected to a connector block within a "header" 303 of the IMD 301. Similarly, in an example, a second output node 308B can be selectively connected to one of the first or second supply nodes, such as through a respective third switch 302C, or a fourth switch 302D. For example, the second output 308B can also be made available outside a housing of the IMD 301, such as via the feed-through, and connected to a separate portion of the connector block within the header 303, or to a separate connector block at least partially contained within the header, etc.

In an example, one or more implantable lead conductors can be connected to the respective first or second outputs 308A-B, such as a respective first lead conductor 310A, or a respective second lead conductor 310B, using one or more connector blocks included at least partially within the header 303, or using one or more other electrical or mechanical connections. In an example, the first and second lead conductors 310A-B can be included within a commonly-shared intravascular lead assembly 311, such as a single-pass defibrillation lead configured for percutaneous intravascular delivery to a location within the heart, such as following a trans-femoral or sub-clavian approach. In an example, the first and second lead conductors 310A-B can be included within a subcutaneous lead assembly, such as configured for implantation in a subcutaneous location between the skin and one or more ribs.

In the example of FIG. 3A, the first and second lead conductors can be connected to one or more distal electrodes. For example, the first lead conductor 310A can be connected to a first implantable electrode 312A, such as located at or near the atrial region of the heart 314 (e.g., a coil located within or near the superior vena cava (SVC), or within the atrium, or elsewhere). Similarly, in an example, the second lead conductor 310B can be connected to a second implantable electrode 312B, such as located at or near a ventricular region of the heart 314, (e.g., a coil located along the length of the implantable lead assembly 311, such as near the apical region of the right ventricle, or elsewhere).

In an example, the first and second electrodes 312A-B can be used for delivery of a defibrillation countershock, such as by using the first, second, third, or fourth switches 302A-D. However, in an example, one or more other electrodes can be used. For example, a lead assembly can be connected to an output circuit block, such as within the IMD 301, and delivered to another cardiac location such as the ostium of the coronary sinus or elsewhere. In another example, a lead assembly can be routed to the pericardial space, such as connected to one or more epicardially-located electrodes. However, such locations can still have limitations, such as only providing defibrillation energy between the distally-located electrodes. In an example, the provide a wider variety of possible pathways or "vectors," a third output node 312C can be used, such as connected to a conductive portion of a housing of the IMD 301 (e.g., providing a "can" pathway). In an example, a fifth switch 302E and a sixth switch 302F can provide a connection between the respective first and second supply nodes and the third output node 312C, such as to provide the illustrative example of the bi-phasic shock waveform 325 of FIGS. 3A-B.

In an illustrative example, as shown in FIG. 3A, the conductive states of the first, second, fifth, and sixth switches 302A-B, and 302E-F can be controlled such as according to the diagram of FIG. 3B, to provide the bi-phasic shock waveform 325. In FIG. 3B, a first plot "A," can show a logical representation of a control signal provided to the first switch 302A (such as to a voltage-controlled input as shown in FIGS. 1-2). In plot "A," when the low level is shown (e.g., a logic "low" or "0"), the first switch 302A can be open. Similarly, in a second plot "B," a third plot "E," and a fourth plot "F," the states of the second switch 302B, the fifth switch 302E, and the sixth switch 302F can be shown.

The plots "A," "B," "E," and "F" can correspond to control signals, such as provided by a controller circuit that can be included within the IMD 301, such as the controller circuit of FIGS. 1-2, and 4. In an example, the controller circuit can include a microprocessor and a memory circuit. The microprocessor can include a capability to execute or perform instructions stored in the memory circuit. For example, the microprocessor can include an execution unit having compatibility with one or more instruction sets, such as a Zilog Z80 (tm) instruction set, or an ARC (tm) instruction set, or one or more other instruction sets. In an example, the memory circuit can include one or more of a read-only memory (e.g., a masked ROM), or a static random access memory (SRAM), such as to store one or more of program code to provide instructions to be performed, information about therapy or sensing configuration parameters, or information gathered from one or more sensors included as a portion of the IMD 301, among other information.

Figure 4B:
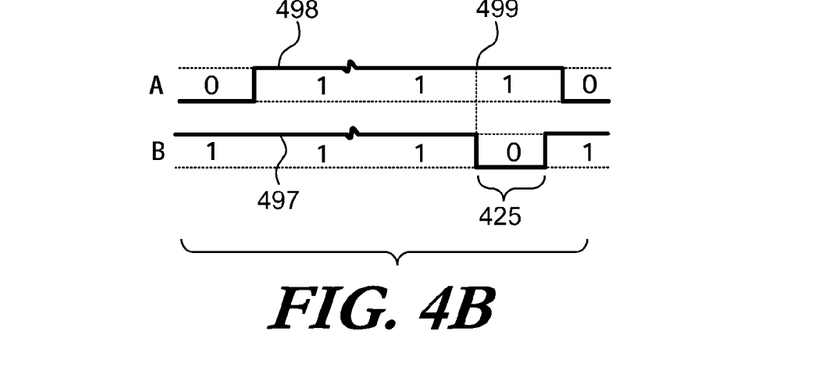

In an example, the defibrillation output circuit can be controlled, such as using a sequence of control signals similar to the illustrative example of FIG. 3B (or modified such as shown in FIGS. 4A-B), such as to provide a defibrillation countershock including a desired waveform (e.g., including one or more pulses having a specified polarity or duration, etc.) between a desired electrode combination (e.g., two or more electrodes). For example, the IMD 301 can use one or more fixed or selectable defibrillation countershock "vectors" or pathways available, such as including a right ventricular coil (RVC)-to-can pathway, as shown in the waveform 325, using the second electrode 312B and the housing connection 312C, or one or more other pathways or electrode configurations, such as based on configuration information stored in the memory circuit.

Other pathways can include a pathway between an SVC electrode (e.g., the first electrode 312A) and the can, or between the SVC electrode and the RVC electrode. In an example, two or more electrodes can be electrically connected together to a commonly-shared supply node, such as to provide a pathway or "vector" between the commonly-shared electrodes and another electrode (e.g., using RVC and SVC tied together, with the housing electrode 312C as the opposing electrode, etc.). In an example, one or more various electrode "vectors" or pathways can be selected automatically by the IMD 301 or manually by a user (e.g., a clinician, physician, or other caregiver) such as depending a type and location of the arrhythmia to be terminated or converted, or in response to previous success or failure in terminating one or more arrhythmias using a similar or different electrode configuration. For example, an SVC-to-can pathway can be used to terminate an atrial arrhythmia. In an example, an (RVC-SVC)-to-can pathway can be used to terminate a supraventricular arrhythmia, etc.

In an example, the "high side" switches, such as the first, third, and fifth switches 302A, 302C, 302E can include electrical ratings similar to the "low side" switches, such as the second, fourth, and sixth switches 302B, 302D, and 302F. But, in an example, to provide a deterministic and predictable transient switching response (e.g., to provide the defibrillation waveform having a specified waveform at a specified instant in time), the high side switches can be switched slightly after low side switches, such as shown in plots "A" and "E." The high side switches can then be used to switch the defibrillation energy by completing the circuit such as to control precisely the instant at which a particular defibrillation pulse is applied (e.g., such as a pulse including a first or second phase as shown in FIG. 3B). In another example, such as an implementation of the output circuit as shown in FIG. 4A, one or more other switches can be turned on or off before, during, or after the high side switching, such as to pre-bias one or more components included in a high side switch driver circuit. For example, the low side switch 302B can be turned on in advance of the high side switch 302A, and the low side switch 302B could be turned off to coincide with or control the turning on of the high side switch 302A, such as shown in the illustrative example of FIG. 4B. In an example, the shock waveform 325 can include one or more pulses having a desired polarity. For example, a waveform having the opposite polarity of the waveform 325 can be provided when the control signals corresponding to plots "A" and "B" are swapped, along with swapping the control signals corresponding to plots "E" and "F." Such swapping can provide a shock waveform between the same electrodes, but with the polarity of each phase reversed. Thus, for illustrative example of FIG. 3B, the fifth switch 302E can instead be used as the high side switch during the first phase of the defibrillation waveform, connecting the housing electrode 312C to a first supply node (e.g., a voltage stored on a capacitor stack), and the second switch 302B can provide a corresponding return path to the second supply node (e.g., the opposite terminal of the capacitor stack) via the second electrode 312B.

FIG. 4A illustrates generally an example of a portion of an implantable defibrillation circuit 400 that can include a first switch 402A and a second switch 402B, and an un-isolated connection (e.g., a solid-state connection, without requiring optical isolation or transformer isolation, etc.) to one or more control outputs such as a first control output 428A and a second control output 428A-B included as a portion of a controller integrated circuit 422. In an example, the circuit 400 of FIG. 4A can be used to controllably connect one of a first supply node 418 (VCAP) or a second supply node 420 (VREF) to an output node 408. In an example, the output node 408 can be configured to connect to an output lead 410, the output lead 410 including an implantable electrode 412A, such as located within or near a heart 414.

The circuitry of the example of FIG. 4A can be similar in function to the output circuit shown in FIG. 1, wherein the first switch 402A is inhibited from connecting the output node 408 to the first supply 418 (VCAP) when the second switch 402B is conducting. Multiple blocks or copies of the circuitry of FIG. 4A can be included in an IMD, such as shown in FIGS. 2, and 3A-B, such as to provide respective output switching blocks corresponding to each defibrillation electrode (e.g., to provide an output "bridge"). For example, a second implantable electrode 412B can be located elsewhere, such as within or near the heart, such as controllably connected to the VCAP or VREF nodes, such as through an output circuit similar to the circuit 400. In FIG. 4A, the first and second switches 402A-B can be insulated gate bipolar transistors (IGBTs), however one or more other switching devices can be used. For example, the "high side" IGBT, such as the first switch 402A can have a forward current rating at or in excess of about 80 Amperes, and a reverse breakdown rating at or in excess of 1 kiloVolt (e.g., to protect the first switch 402A from a shock applied to a patient externally, or to provide a specified margin above the normal operating voltage range of the capacitor stack 426, etc.). In an example, one or more of the first or second switches 402A-B can have a lesser forward current rating, such as meeting or exceeding about 40 Amperes, such as when the impedance presented to the output circuit 400 at the output node 408 is greater than or equal to 20 Ohms, and the voltage stored on the capacitor stack 426 is at about 800 Volts or less.

In the example of FIG. 4A, one or more other components can be used to provide solid-state control of the first and second switches 402A-B by the controller integrated circuit 422, without requiring an opto-isolator, triggering transformer, or a transformer-coupled supply, as may be required by other approaches. The example of FIG. 4A includes a first rectifier 404, a second rectifier 434, a capacitor 432, and a series resistor 430.

FIG. 4B shows an illustrative example of the relative timing of control signals that can be provided to the first and second switches 402A-B, such as by the first and second control outputs 428A-B, to turn on or "fire" the first switch 402A (e.g., the "high side" switch). Initially, before turning on the first switch 402A, a current path or voltage bias path can be provided. In an example, the bias path can be provided by the second switch 402B (e.g., the second switch 402B can be turned on initially, such as using a logic "high" potential provided by the second control output 428B). In addition, or instead of using the switch 402B, the bias path can include a path through heart 414 tissue such as including the second electrode 412B connected to the VREF node (e.g., 0V, such as connected to a lower terminal of a capacitor stack 426, and referenced to the lower terminal, such as biased through another "arm" or output circuit block similar to the circuit 400). In these examples, the bias path can provide a voltage at or near the potential of the second supply node 420 (VREF), at the emitter of the first switch 402A.

In an example, a first control waveform 498, corresponding to a state of the first control output 428A, can transition from a logic "low" to a logic "high," such as to charge the capacitor 432 to approximately 12V (e.g., at or near the logic "high" potential). During or after the capacitor 432 charging, a second control waveform 497, corresponding to a state of the second control output 428B, can be at logic "high," to allow charging of the capacitor 432. In the example of FIGS. 4A-B, the second control output 428B and the second switch 402B can be used to trigger the first switch 402A (e.g., to turn on the first switch 402A). At 499, the second control waveform 497 can transition from a logic "high" to a logic "low," and the voltage stored on the capacitor 432 can be impressed across the gate-emitter portion of the first switch 402A, through the resistor 430, and in parallel with the first rectifier 404, turning on the first switch 402A (e.g., biasing the IGBT 402A into conduction).

During the time when the first switch 402A is conducting, the voltage across a gate-emitter portion of the first switch 402A can be controlled or maintained, such as by using a controlled voltage provided by the first rectifier 404 (e.g., in a reverse breakdown region of operation of the first rectifier). For example, the second rectifier 434 prevents the capacitor 432 from discharging back into the first control output 428A, and allows the output node 408 to rise to the VCAP voltage of the first supply node 418 while still maintaining the specified gate-emitter voltage across the first rectifier 404.

In an example, the rise-time of the voltage at the gate 416 can also be controlled, such as using a time constant determined by a filter circuit (e.g., a resistor-capacitor or RC time constant). In the example of FIG. 4A, the filter circuit can include the resistor 430, and the time constant can be determined by the combination of the resistor 430 and the gate capacitance of the first switch 402A. The first switch 402A can remain turned on during a specified interval where both the first control output 428A is at logic "high," and the second control output 428B is at logic "low," such as during a specified interval 425 as shown in FIG. 4B. In an example, after being turned on, the first switch 402A can then be turned off, such as when the second control waveform 497 transitions from a logic "low," back to a logic "high" at the end of the specified interval 425. Thus, the first switch 402A can be controlled using a commonly-shared path including the first output node 408, the second supply node 420 (VREF), and the first rectifier 404.

In an example, the circuit 400 can be used to provide a return path for a defibrillation countershock during at least a portion of a defibrillation countershock delivery or to pre-bias another different output circuit 400 used for another different electrode (e.g., to bias another "arm," as discussed above), such as by turning on the second switch 402B. For example, the second electrode 412B can be controllably connected to the first supply node 418 (VCAP), and the second switch 402B, when closed, provides a current path through the heart 414, through the first output node 408, through the second switch 402B, back to the capacitor stack 426, to complete the circuit for providing at least a portion of a defibrillation countershock waveform.

In an example, one or more of the first and second control outputs 428A-B can include a third state that is neither logic "high" or logic "low," such as where each respective control output presents a high output impedance, such as to conserve energy when the output circuit 400 is not being used). In the example of FIG. 4A, one or more additional rectifiers can be included, such as a third rectifier 436, or a fourth rectifier 438. Though not required, the third and fourth rectifiers 436, 438 can provide additional protection such as to prevent backcharging of the capacitor stack 426, or to protect the first and second switches 402A-B from voltage spikes, such as due to a flyback effect during switching caused at least in part by the parasitic inductance of the loop formed by the output node 408, lead 410, or other circuitry or conductors.

In one approach, one or more thyristors can be used for the first or second switches 402A-B instead of the one or more IGBTs, such as including a gate-turn-off (GTO) thyristor (e.g., a remote gate thyristor (RGT) or other GTO-type device) having a relatively large reverse-voltage blocking capability (e.g., around 1 kiloVolt). However, GTOs generally can be more sensitive to sudden changes in forward current during switching. For example, when a GTO is turned on, if the rise-time of a gate signal controlling the GTO is not limited, the GTO can be damaged or destroyed during switching of relatively high currents (e.g., current for a defibrillation countershock). Similarly, if the forward voltage of the GTO is not controlled during turn off, the GTO can be damaged or destroyed.

Such damage or destruction can occur because the GTO needs a finite amount of time to become highly conductive or to pinch off conduction. A large transient forward current (e.g., a current having a relatively high dI/dt) can be outside of the GTO's safe operating area (e.g., outside a range of operating currents and frequencies over which the GTO is relatively reliable, such as related to a specified maximum junction temperature of the GTO). For example, when a gate signal rise-time is too rapid, forward current flow through the GTO can increase correspondingly rapidly. But, the initial current flow can be concentrated in a relatively small area of the GTO die leading to localized thermal damage (e.g., exceeding the GTO's rated junction temperature). To prevent such damage, a driver circuit can be used to adjust or limit the rise-time or fall-time of the gate signal to protect the GTO.

The present inventors have recognized that using one or more IGBTs, such as instead of the one or more GTOs, can reduce cost or complexity of the output circuit. For example, the gate input of the IGBT can be less sensitive to rise-time, and thus a control signal having a carefully controlled rise-time need not be used, allowing a reduction in component count as compared to using the GTO. Also, IGBTs having a specified current rating and reverse breakdown rating can generally be lower in cost than similarly-rated GTO devices. In an example, an IGBT can use a simpler and more compact substrate layout (e.g., requiring fewer interconnects on the under-side of an exemplary IGBT die), such as a substrate included in a module or device package housing the defibrillation output circuit, such as discussed below in the example of FIGS. 5A-B.

The present inventors have also recognized that using one or more IGBTs can provide a more compact assembly, such as instead of using one or more field-effect transistors. For example, a FET having comparable reverse breakdown, forward current, and forward "on" resistance characteristics can be generally larger in surface area than a corresponding IGBT.

Figure 5A:
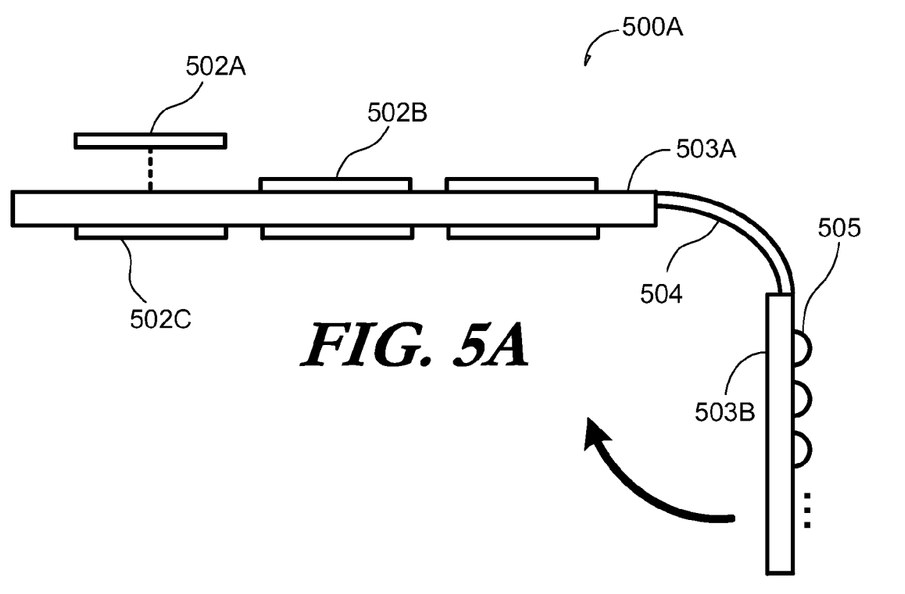
FIGS. 5A-B illustrate generally an example of a module including at least a portion of the defibrillation output circuit.
Figure 5B:
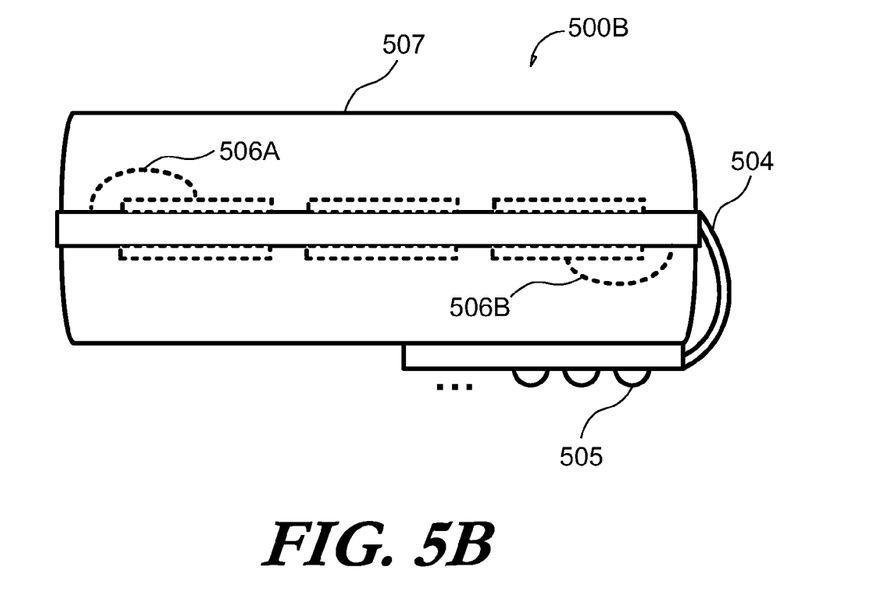

FIGS. 5A-B illustrate generally an example of a module 500A-B including at least a portion of the implantable defibrillation output circuit, such as including the circuit 400 of FIG. 4. In FIGS. 5A-B, the module 500A-B can be a surface-mount technology (SMT) assembly, such as including a pin array, a land array, ball grid array (e.g. including one or more solder balls or bumps, such as a first ball 505), or including another mechanical bonding or electrical interconnection scheme. For example, the module 500A-B can be a multi-chip module, such as including two or more semiconductor dice or other parts or components, and corresponding interconnects, such as attached to or using a non-semiconductor substrate. In an example, such as shown in FIG. 5A, a substrate can be provided, such as including a first portion 503A, a second portion 504, or a third portion 503B. In an example, one or more IGBTs such as used for the first, second, or other switches of FIGS. 1-2, 3A-B, 4A-B can be mounted on the first portion 503A (or elsewhere). For example, a first IGBT 502A, a second IGBT 502B or a third IGBT 502C can each be separate semiconductor dice each mounted on a commonly-shared non-semiconductor substrate, such as on the first portion 503A, along with one or more other components (e.g., shown in FIG. 4), such as using solder, conductive epoxy, or one or more wire bonds, such as a first wire bond 506A or a second wire bond 506B (e.g., using aluminum, copper, gold, etc.).

In an example, the first portion 503A, the second portion 504, or the third portion 503B can include an organic or ceramic substrate material, such as a flexible or rigid substrate material (e.g., a polyimide material, a glass-epoxy laminate, a bismaleimide triazine (BT) laminate, a high or low temperature co-fired ceramic material, or another material) or a combination of rigid and flexible materials. In an example, during or after components have been attached to the first portion 503A of the module 500A, the first portion 503A, second portion 504, or the third portion 503B can be at least partially surrounded by an encapsulant 507, such as using one or more of a molding operation, a dam-and-fill operation, or other technique, such as including a thermosetting material (e.g., epoxy) or thermoplastic material. For example, the encapsulant can provide one or more of a hermetic seal isolating the IGBTs 502A-C or one or more other components from moisture or other contaminants, or to provide enhanced high-voltage isolation (e.g., to suppress or reduce dielectric breakdown). In an example, the second portion 503B can be rotated such as provided by the second portion 504, to provide a more compact module 500B. The one or more solder bumps or solder balls, such as the ball 505, can be used to attach the module 500B to another assembly, such as using reflow-soldering or one or more other process steps.

In an example, if one or more GTO devices are used instead of the one or more IGBTs 502A-C, a GTO device die (e.g., such as remote gate thyristor) can have a mesa-like structure, and can include multiple metal connections on a bottom side of the GTO device. The mesa-type construction can make the GTO more sensitive to mechanical damage as compared to a primarily planar-style device (e.g., chips at the periphery of the die or other damage to a die passivation can affect electrical performance). Such construction can therefore impact yield during manufacturing, and can reduce manufacturing flexibility by limiting the pool of available suppliers. The multiple metal connections on the bottom side of the GTO can make the package design for a multi-chip package (e.g., shown in FIGS. 5A-B) more complex as compared to using other types of switching devices. For example, adjacent metal pads can be inadvertently bridged during reflow-soldering, or by conductive epoxy, during manufacturing. In contrast, the present inventors have recognized, among other things, IGBTs, such as one or more of the first-third IGBTs 502A-C can have a single collector connection (rather than multiple connections) on the portion of the IGBT facing the first portion 503C of the module substrate. In an example, when two or more of the IGBTs are used as "high side" switches, their respective collector connections can be commonly shared, such as to simplify the layout of one or more metal regions on or within the first portion 503A of the module.

Figure 6:
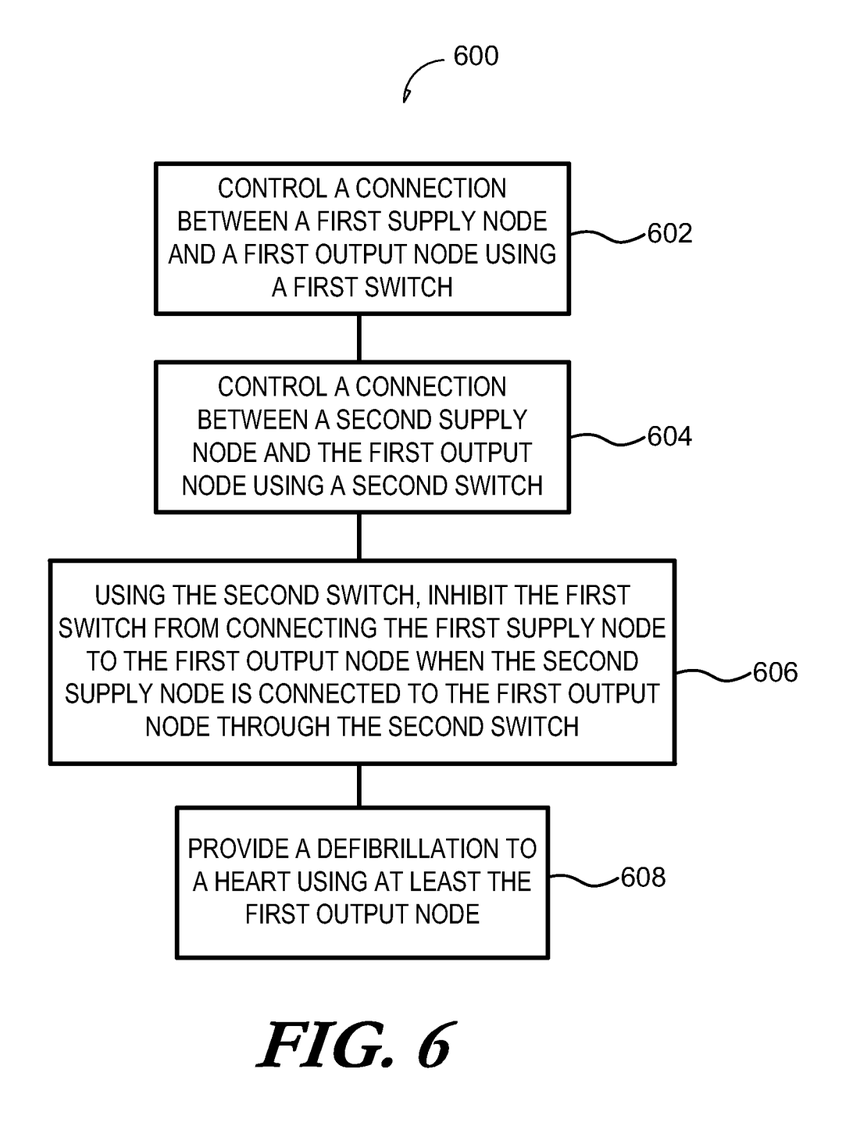
FIG. 6. illustrates generally an example of a method for controlling a first switch and a second switch, such as included in the defibrillation output circuits of one or more of FIGS. 1-2, 3A-B, 4A-B, or 5A-B.

FIG. 6. illustrates generally an example of a method 600, such as for controlling a first switch and a second switch, such as included in the defibrillation output circuits of one or more of FIGS. 1-2, 3A-B, 4A-B, or 5A-B.

At 602, in an example, a connection between a first supply node and a first output node can be controlled, such as using a first switch. At 604, in an example, a connection between a second supply node and the first output node can be controlled using a second switch. The first and second switches can include one or more IGBTs or other switching circuitry or devices, such as discussed in the examples of FIGS. 1-2, 3A-B, 4A-B, or 5A-B. For example, at 606, the second switch can be used to inhibit the first switch from connecting the first supply node to the first output node when the second supply node is connected to the first output node through the second switch.

In an example, at 608, a defibrillation countershock can be provided to a heart using at least the first output node. For example, an output circuit can include one or more blocks such as shown in FIG. 1 or 4A-B, such as to provide a defibrillation countershock waveform having a specified initial voltage, number of phases, duration of each phase, interphase delay, etc.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile tangible computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

The claimed invention is:

1. An implantable apparatus, comprising:
    an implantable electrostimulation therapy output circuit, including:
        a first defibrillation supply node;
        a first defibrillation output node;
        a second defibrillation supply node;
        a first rectifier;
        a first switch having a control input configured to control a conductive state of the first switch, the first switch coupled to the first defibrillation supply node and the first defibrillation output node, and the first switch configured to controllably connect the first defibrillation supply node to the first defibrillation output node;
        a second switch coupled to the second defibrillation supply node, the control input of the first switch, and the first output node, the second switch configured to controllably connect the second defibrillation supply node to the first defibrillation output node through the first rectifier;
        wherein the second switch is configured to inhibit the first switch from connecting the first defibrillation supply node to the first defibrillation output node when the second defibrillation supply node is connected to the first defibrillation output node through the second switch; and
        wherein the first output node is configured to be coupled to a first implantable electrode to provide a defibrillation therapy to a heart.

2. The implantable apparatus of claim 1, wherein the the control input of the first switch is configured to control a conductive state of the first switch in response to a voltage provided to the control input; and
    wherein the second switch is configured to controllably connect the second defibrillation supply node to the control input of the first switch when the second switch connects the second defibrillation supply node to the first defibrillation output node.

3. The implantable apparatus of claim 2, further comprising a filter circuit coupled to the control input, the filter circuit configured to adjust at least one of a rise-time or a fall-time of the first switch, at least in part using a capacitance of the control input.

4. The implantable apparatus of claim 1, further comprising:
    an energy source configured to provide defibrillation energy to the first and second defibrillation supply nodes at a specified initial voltage at the first defibrillation supply node that is greater than or equal to 780 volts with respect to the second defibrillation supply node.

5. The implantable apparatus of claim 1, wherein the implantable electrostimulation therapy output circuit further includes:
    a second rectifier;
    a second defibrillation output node;
    a third switch having a control input configured to control a conductive state of the third switch, the third switch coupled to the first defibrillation supply node and the second defibrillation output node and configured to controllably connect the first supply node to the second defibrillation output node;

a fourth switch coupled to the second defibrillation supply node, the control input of the third switch, and the second defibrillation output node, the fourth switch configured to controllably connect the second defibrillation supply node to the second defibrillation output node through the second rectifier;

wherein the fourth switch is configured to inhibit the third switch from connecting the first defibrillation supply node to the second defibrillation output node when the second defibrillation supply node is connected to the second defibrillation output node through the fourth switch; and wherein the second output node is configured to be coupled to a second implantable electrode.

6. The implantable apparatus of claim 5, wherein each of the respective first, second, third, and fourth switches comprises an insulated gate bipolar transistor (IGBT).

7. The implantable apparatus of claim 5, wherein the implantable electrostimulation therapy output circuit is configured to provide an electrostimulation therapy waveform across the first and second defibrillation output nodes, the electrostimulation therapy waveform having a specified polarity when only one of the first or second switches is turned on and only one of the third or fourth switches is turned on.

8. The implantable apparatus of claim 7, wherein the implantable electrostimulation therapy output circuit is configured to provide a electrostimulation therapy having a first polarity during a first portion of the electrostimulation therapy waveform and a second opposite polarity during a second portion of the electrostimulation therapy waveform.

9. The implantable apparatus of claim 5, further comprising:

a control circuit;

wherein the first, second, third, and fourth switches each include a respective control input, and wherein each respective control input is coupled to the control circuit using respective un-isolated electrical couplings.

10. The implantable apparatus of claim 5, further comprising a commonly-shared substrate;

wherein each of the first, second, third, and fourth switches are separate semiconductor dice positioned on the commonly-shared substrate.

11. The implantable apparatus of claim 10, wherein the commonly-shared substrate comprises a printed circuit board (PCB).

12. The implantable apparatus of claim 10, wherein the commonly-shared substrate comprises a non-semiconductor material.

13. The implantable apparatus of claim 12, wherein the commonly-shared substrate further comprises respective solder conductors coupled respectively to the first and second defibrillation supply nodes and the first and second defibrillation output nodes, the respective solder conductors configured to mechanically and electrically coupled the commonly-shared substrate to a printed circuit board.

14. The implantable apparatus of claim 13, wherein the respective solder conductors further comprise a ball grid array (BGA) arrangement.

15. The implantable apparatus of claim 13, wherein the respective solder conductors further comprise a land grid array (LGA) arrangement.

16. The implantable apparatus of claim 1, further comprising an implantable lead including the first electrode, the first electrode coupled to the first defibrillation output node.

17. The implantable apparatus of claim 1, further comprising a housing including a conductive portion, and wherein the conductive portion comprises the first implantable electrode.

18. The implantable apparatus of claim 1, wherein the implantable therapy output circuit comprises an implantable defibrillation circuit configured to provide a defibrillation waveform using the first and second switches.

19. An implantable apparatus, comprising:

an implantable electrostimulation therapy output circuit including:

a first supply node;

a first output node;

a second supply node;

a first rectifier;

a control circuit;

a first switch having a control input configured to control a conductive state of the first switch using a voltage, the first switch coupled to the first supply node and the first output node, and the first switch configured to controllably connect the first supply node to the first output node; and a second switch coupled to the second supply node, the control input of the first switch, and the first output node, the second switch configured to controllably connect a second supply node to the first output node through the first rectifier and configured to controllably connect the second supply node to the control input of the first switch;

wherein the second switch is configured to inhibit the first switch from connecting the first supply node to the first output node when the second supply node is connected to the first output node through the second switch; and wherein the first output node is configured to be coupled to a first implantable electrode; and wherein the control input is coupled to the control circuit using an un-isolated electrical coupling.

20. The implantable apparatus of claim 19, further comprising a housing including a conductive portion, and wherein the conductive portion comprises the first implantable electrode.

* * * * *